United States Patent [19]
Horowitz et al.

[11] Patent Number: 5,342,659
[45] Date of Patent: Aug. 30, 1994

[54] METHOD OF GRAFTING POLYMERIZABLE MONOMERS ONTO SUBSTRATES

[75] Inventors: Carl Horowitz, Brooklyn; Mohan Sanduja, Flushing; Paulose Thottathil, New Hyde Park, all of N.Y.

[73] Assignee: Polymer Research Corp. of America, Brooklyn, N.Y.

[21] Appl. No.: 31,118

[22] Filed: Mar. 12, 1993

Related U.S. Application Data

[63] Continuation-in-part of Ser. No. 780,102, Oct. 21, 1991, Pat. No. 5,232,748.

[51] Int. Cl.$^5$ .............................................. B05D 3/06
[52] U.S. Cl. .................................... 427/553; 427/302; 427/303; 427/322; 427/399; 427/554
[58] Field of Search ............... 427/302, 303, 322, 399, 427/553, 554

[56] References Cited

U.S. PATENT DOCUMENTS

| | | | |
|---|---|---|---|
| 3,401,049 | 9/1968 | Horowitz | 427/302 |
| 4,003,701 | 1/1977 | Brickman | 8/115.6 |
| 4,960,611 | 10/1990 | Fujisawa et al. | 429/451 X |
| 5,013,338 | 5/1991 | Anand et al. | 427/488 X |
| 5,137,758 | 8/1992 | Kistner et al. | 427/350 |

*Primary Examiner*—Michael Lusignan
*Attorney, Agent, or Firm*—Steinberg, Raskin & Davidson

[57] ABSTRACT

The invention relates to the chemical bonding of a polymer or polymers onto a non-metallic substrate such as cellophane by contacting the substrate with a grafting solution that contains monomers, prepolymers, catalysts and possibly other ingredients, to obtain graft polymerization onto the substrate with intimate bonding of the polymer onto the substrate surface, and curing the polymer on the substrate by microwave, laser or ultrasonic energy. The invention provides a method where the bonding of the polymer is effected solely by physical rather than chemical means by eliminating the use of silver nitrate in the pretreatment step and using microwave, laser or ultrasonic energy to polymerize the monomers and binding the resulting polymer to the substrate, with the resulting grafted polymer having the same characteristics as if the bonding was effected chemically with silver ions or colloidal silver.

17 Claims, No Drawings

METHOD OF GRAFTING POLYMERIZABLE MONOMERS ONTO SUBSTRATES

CROSS-REFERENCE TO RELATED APPLICATION

This is a continuation-in-part of our copending application Ser. No. 07/780,102 filed on Oct. 21, 1991, now U.S. Pat. No. 5,232,748.

BACKGROUND OF THE INVENTION

Polymers have been grafted onto non-metallic substrate surfaces, such as cellophane, for example, as described in U.S. Pat. No. 3,401,049. The basic process of grafting of the polymer comprises the contacting of the non-metallic body, for example, with a solution of silver nitrate and an alkali metal hydroxide, then contacting the thus treated body with a polymerizable composition of a polymerizable monomer and a catalyst, the polymerization taking place directly on the molecules of the substrate. As described in U.S. Pat. No. 3,401,049, the polymerization can take place at room temperature, in which case, considerable time is required, or it can be accelerated by heat.

In more recent processing, the grafting of the polymer onto the substrate has utilized radiation, corona discharge, UV treatment and thermal treatment to accelerate the polymerization and cure the polymer. The processing is in general the same, namely the surface of the substrate activated by the reaction of silver nitrate with, e.g. sodium hydroxide is brought into contact with a grafting solution which contains the monomers, prepolymers, catalyst and graft initiator system, and the resulting graft treated surface is then subjected to cure as set forth above.

However, all of the methods are either too hazardous, such as grafting by means of radiation, or too time and energy consuming, such as grafting by UV or thermal treatment.

In the most recent processing, as set forth in our copending application Ser. No. 07/780,102, the grafting of the polymer onto the substrate proceeded in the same manner, however with the use of microwave or laser energy to accelerate the polymerization and grafting of the resulting polymer onto the surface of the substrate.

SUMMARY OF THE INVENTION

We have discovered that it is possible to effect the grafting of a polymer onto a substrate without the need for the silver nitrate—sodium hydroxide reaction, provided that the polymerizable composition of monomer or prepolymer and polymerization activator, such as a catalyst, is subjected to microwave or laser energy or ultrasonic energy to accelerate the polymerization. This causes grafting of the resulting polymer onto the surface of the substrate without the presence of silver ions or colloidal silver.

In accordance with the present invention the non-metallic substrate is directly brought into contact with a polymerizable composition of monomer or prepolymer and a polymerization activator, such as a catalyst, and is subjected to microwave, laser or ultrasonic energy to cause polymerization and grafting of the resulting polymer onto the surface of the substrate.

It is accordingly a primary object of the present invention to provide a method of polymerizing and grafting polymerizing monomers onto non-metallic substrates in the absence of silver ions or colloidal silver.

It is another object of the present invention to provide a method of polymerizing polymerizable monomers and grafting the resulting polymers onto non-metallic substrates by means of microwave, laser or ultrasonic energy.

Other objects and advantages of the present invention will be apparent from a further reading of the specification and of the appended claims.

The present invention is applicable to grafting of polymers onto a wide variety of non-metallic materials such as cellophane, cotton fibers and fabrics, rayon fibers and fabrics, wood, nylon fibers, fabrics and films, fibers, fabrics, and other films, polyethylene glycol adipate films, cellulose triacetate fibers, fabrics and films, polyolefine fibers and fabrics, natural and synthetic rubbers, leather, wool, hair, animal and human skin, bone, teeth, body tissues, glass, paper and many others.

For purposes of simplicity, the invention will be in general be described with respect to the treatment of cellophane as the substrate. The invention is applicable to the use of any polymerizable monomer or prepolymer such as: vinylidene chloride, chloroprene, isoprene, dimethylaminoethyl methacrylate, styrene, 1,3-butylene dimethacrylate, hydroxyethyl methacrylate, isoctylvinyl ether, acrylonitrile, acrylamide, N-vinyl pyridine, glycidyl methacrylate, N-vinyl caprolactam, N-vinyl pyrrolidone, N-vinyl carbazole, acrylic acid, methacrylic acid, ethyl acrylate, ethyl methacrylate, itaconic acid, isobutylmethacrylate, methyl acrylate, sodium styrene sulfonate, sodium vinyl sulfonate, bis (betachloroethyl) vinyl phosphate, cetyl vinyl ether, divinylether of ethylene glycol, divinyl ether of butanediol, vinyl toluene, vinyl acetate, octadecyl vinylether. Also amines can be quaternized with benzyl chloride, ethyl iodide, methyl or ethylsulfate. Conversely, monomeric chlorides can be quaternized with tertiary amines to give quaternary ammonium compounds. Some suitable tertiary amines are: n-ethyl morpholine, pyridine, cetyldimethyl pyridine, methylmethacrylate.

In accordance with the invention, a cellophane sheet is not pretreated with graft activating solution having silver nitrate. The sheet is directly dipped into a polymerizable composition containing monomers, polymer catalyst and other ingredients. The composition is adapted to be activated to polymerization. The cellophane sheet is then air dried and subjected to microwave, laser or ultrasonic energy whereby polymerization is caused and the resulting polymer is physically bonded to the surface of the substrate.

In accordance with a preferred embodiment of the invention, the non-metallic substrate is contacted with an alkali metal hydroxide prior to being dipped into the polymerizable composition.

The monomer can be dissolved in a suitable solvent such as dimethylformanide, tetrahydrofurane, tetrahydrofurfuryl alcohol, dimethylsulfoxide, water, methyl, ethyl or isopropyl alcohol, acetone, methyl ethyl ketone and ethyl acetate. Also mixtures of two or more of the above can be used.

Among the catalysts which can be used are: ammonium persulfate, hydrogen peroxide, tert-butylhydroperoxide, ditertbutyl peroxide, benzoyl peroxide, dicumyl peroxide, lauroyl peroxide, tert-butyl perbenzoate and peracetic acid. A combination of two or more monomers mentioned above can be grafted to obtain graft copolymers.

The concentration of the monomer in the solution can vary within practically any limits, for example, from between about 0.1% to 50%. However, the preferred concentration for facility of use is between about 5% and 15% by weight of the solution. In the case of acceleration of the polymerization by microwave treatment, the treatment time is between about 2-5 minutes. In the case of the use of laser energy to accelerate the graph polymerization, the time of treatment is shortened to less than one second up to about 30 seconds and possibly up to one minute.

In the case of the use of ultrasonic energy for the graft polymerization, the treatment time may be up to about 30 minutes.

Thus the overall method of the present invention comprises pretreating the cellophane sheet or film with a graft activating solution containing no silver nitrate but containing sodium or potassium hydroxide. The sheet is then treated by dipping into a monomer-catalyst solution. This is followed by polymerization of the monomers onto the sheet by application of microwave energy for 2-5 minutes, laser energy for up to one minute or ultrasonic energy up to about 30 minutes whereby polymerization is caused and the resulting polymer is physically bonded to the cellophane sheet.

DESCRIPTION OF PREFERRED EMBODIMENTS

The following examples are given to further illustrate the invention. The scope of the invention is not, however, meant to be limited to the specific details of the examples.

The following is a general description of the method:

Graft coating compositions are prepared and each one is applied onto pre-activated cellophane film by dipping. The resulting monomer treated cellophane film is subjected to curing in a microwave oven for 2-5 minutes or by laser energy for up to one minute or by ultrasonic energy for up to about 30 minutes. The grafted cellophane film which is thus prepared is tested by adhesion, percent add-on, leaching with plain water and other characteristics. Before treating the cellophane with the monomer solution, the substrate is activated with graft activating solution, rinsed with water and air dried.

The graft coating composition does not contain any silver nitrate and the polymerization and binding step is effected by microwave, laser or ultrasonic energy.

The following are the steps involved in the grafting of cellophane film according to the preferred method:

I. Pretreatment Step—Treatment of Cellophane Film with Graft Activating Solution. The steps involved in the treatment of cellophane film with graft activating solution are as follows:
1. Wash with water at ambient temperature for one minute.
2. Rinse in water at room temperature for 10-15 seconds.
3. Dip in 1% potassium hydroxide solution maintained at 80° C. for one minute.
4. Wash in water.
5. Subject to air dry.

II. Preparation of Monomer-Solution-Grafting Solution.

Into 100 ml of water in a container are added the following ingredients:
dimethyl formamide
monomer mixture
ammonium persulfate
sodium metabisulfite The contents are stirred to a uniform solution.

III. Grafting of monomer solution onto Cellophane Film:

A 8×11″ cellophane sheet was pretreated with graft activating solution in accordance with the steps indicated in (I) above. The dry pretreated film was washed with water and then dipped into monomer solution prepared in (II) above. The monomer treated cellophane film was air dried for few minutes and then subjected to cure in a microwave oven for 2-5 minutes or by laser for 30 seconds or by ultrasonics for up to 30 minutes. The graft, cellophane films thus prepared were then tested for various characteristics.

EXAMPLE I

I. Preactivating Solution:
solution A—wash with plain water at room temperature for one minute.
Solution B—rinse in water at room temperature for 10 seconds.
Solution C—dip in 1% potassium hydroxide solution at 80 CC for one minute.
Solution D—wash in plain water and dry.

II. Grafting Solution:

|  | Parts by Weight |
| --- | --- |
| Water | 100.00 |
| Dimethylformanide (DMP) | 20.00 |
| Hydroxyethylmethacrylate | 8.00 |
| Acrylonitrile | 2.00 |
| Ammonium persulfate | 1.00 |
| Sodium metabisulfite | 1.00 |

Preactivated cellophane sheet was dipped in this solution, air dried and subjected to cure in a microwave for 5 minutes or by laser for 45 seconds.

The grafted cellophane which was clear and transparent, exhibited an increase in weight of 17.54%.

The example was repeated with the curing being effected by ultrasonics for about 30 minutes. The increase in weight was similar to that obtained by laser or by microwave.

EXAMPLE II

I. Preactivating solution is the same as in Example I.
II. Grafting Solution:

|  | Parts by Weight |
| --- | --- |
| Water | 100.00 |
| Dimethyl formamide | 20.00 |
| Acrylonitrile | 2.00 |
| 2-acrylamido 2 methylpropane sulfonic acid (AMPS) | 8.00 |
| Ammonium persulfate | 1.00 |
| Sodium metabisulfite | 1.00 |

The cellophane sheet after dipping was air dried and subject to cure by laser for 30 seconds. The resulting grafted sheet was clear and transparent and exhibited an increase in weight of 17.20%.

EXAMPLE III

I. Preactivating solution is the same as in Example I.
II. Grafting Solution:

|  | Parts by Weight |
| --- | --- |
| Water | 150.00 |
| Dimethylformamide (DMF) | 30.00 |
| 2-acrylamide-2-methylpropane sulfonic acid (AMPS) | 12.00 |
| Hydroxyl ethyl methacrylate | 3.00 |
| Ammonium persulfate | 1.50 |
| Sodium metabisulfite | 1.50 |

The grafted cellophane sheet exhibited a weight increase of 18.47%.

Cellophanes were washed after grafting in monomer solution which was cured using microwave, laser beam, or ultrasonic vibration.

| CONTROL | AFTER GRAFTING | % ADD-ON | AFTER WASHING | % ADD-ON |
| --- | --- | --- | --- | --- |
| TWO MINUTES IN MICROWAVE | | | | |
| A. 0.252 | 0.297 | 17.85 | 0.295 | 17.06 |
| B. 0.188 | 0.226 | 20.12 | 0.222 | 18.08 |
| C. 0.208 | 0.246 | 18.26 | 0.245 | 17.79 |
| FIVE MINUTES IN MICROWAVE | | | | |
| A. 0.228 | 0.272 | 19.29 | 0.268 | 17.54 |
| B. 0.250 | 0.294 | 17.60 | 0.293 | 17.20 |
| C. 0.222 | 0.264 | 18.91 | 0.263 | 18.47 |
| TWO MINUTES IN LASER BEAM | | | | |
| A. 0.238 | 0.281 | 18.06 | 0.279 | 17.23 |
| B. 0.217 | 0.259 | 19.35 | 0.258 | 18.89 |
| C. 0.226 | 0.270 | 19.46 | 0.267 | 18.16 |
| FIVE MINUTES LASER BEAM | | | | |
| A. 0.252 | 0.298 | 18.25 | 0.296 | 17.46 |
| B. 0.236 | 0.281 | 19.06 | 0.279 | 18.22 |
| C. 0.247 | 0.293 | 18.62 | 0.292 | 18.22 |
| THIRTY MINUTES ULTRASONIC | | | | |
| A. 0.212 | 0.243 | 14.62 | 0.241 | 13.67 |
| B. 0.236 | 0.273 | 15.68 | 0.270 | 14.40 |
| C. 0.228 | 0.261 | 14.47 | 0.259 | 13.60 |

Testing of Grafted Cellophane Sheet—Adhesion and Percent Add—On (Increase in Weight).

1. Adhesion

A piece of Scotch Brand Cellophane was implanted firmly against a grafted cellophane film and then pulled upward sharply. No visual delamination of the grafted polymer film from base material cellophane sheet was observed. This indicated that grafting of polymerizable monomer to a polymer onto cellophane sheet was strongly bonded chemically.

2. Percent Add On—Increase in Weight of Grafted Cellophane Sheet: The grafted cellophane sheet was estimated for increase in weight with respect to control (non-grafted cellophane sheet). The increase in weight in each case is given in Table I.

TABLE I

Increase in weight of grafted and non-grafted cellophane sheet.

| Examples | Increase in Weight Grafted Cellophane Sheet (0/0) | Increase in Weight Non-Grafted Cellophane Sheet (0/0) |
| --- | --- | --- |
| I | 17.54 | 1.63 |
| II | 17.20 | 2.00 |
| III | 18.47 | 1.46 |

In order to test the durability of increase in weight to grafted cellophane sheet, the grafted cellophane sheet obtained in each example was washed with plain water for 5 minutes at room temperature, air dried and weighed again. The washings were also carried out in case of non-grafted cellophane sheet (control). The results are summarized in Table II.

TABLE II

Weight of Grafted and Non-Grafted Cellophane Sheet After Washings With Plain Water At Room Temperature

| Examples | Weight after Washing Grafted Cellophane Sheet (0/0) | Weight after Washing Non-Grafted Cellophane Sheet (0/0) (Control) |
| --- | --- | --- |
| I | 17.54 | 0.02 |
| II | 17.20 | 0.11 |
| III | 18.47 | 0.10 |

As can be seen from the results in Table II, there is no significant loss in weight of grafted cellophane sheet after washings thereby indicating that the attachment of polymer to the surface of the cellophane sheet is permanent. However, in case of the non-grafted cellophane sheet (control), there is a significant loss in weight after washings. This indicated that the attachment of polymer to non-grafted cellophane film (control) was physical rather than chemical.

We claim:

1. A method of grafting a polymer onto a nonmetallic substrate which comprises:
   directly contacting a non-metallic substrate without pretreatment or pretreated only with an alkali metal hydroxide with a polymerizable composition including monomers or prepolymers and a catalyst and being adapted to be activated to polymerization into a resulting polymer; and
   curing the polymerizable composition by applying microwave, laser or ultrasonic energy to cause polymerization of the monomers or prepolymers and same onto the substrate thus binding the resulting polymer intimately to the substrate.

2. The method of claim 1, and including the steps of:
   pretreating the non-metallic substrate with an alkali metal hydroxide prior to contacting the same with the polymerizable composition.

3. The method of claim 2, and including the step of washing the pretreated substrate with water and then subjecting the substrate to air drying.

4. The method of claim 2, wherein the curing is effected by microwave energy applied for 2–5 minutes.

5. The method according to claim 2, wherein the curing is effected by laser energy applied for up to one minute.

6. The method of claim 2 wherein the curing is effected by ultrasonic energy applied for up to about 30 minutes.

7. The method of claim 2 wherein the substrate is cellophane, cotton, rayon, wood, nylon, polyester, polyethylene glycol, adipate, cellulose triacetate, polyethylene, natural and synthetic rubbers, leather, wool, hair or skin.

8. The method of claim 7, wherein the curing is effected by microwave energy applied for 2–5 minutes.

9. The method of claim 7, wherein the curing is effected by laser energy applied for up to one minute.

10. The method of claim 7, wherein the curing is effected by ultrasonic energy applied for about 30 minutes.

11. The method according to claim 1, wherein the non-metallic substrate is cellophane.

12. The method of claim 2, wherein the non-metallic substrate is cellophane.

13. The method of claim 1, wherein the catalyst is selected from the group consisting of ammonium persulfate, hydrogen peroxide, tertbutylhydroperoxide, ditert-butyl peroxide, benzoyl peroxide, dicumyl peroxide, lauroyl peroxide, tert-butyl perbenzoate and peracetic acid.

14. The method according to claim 1, wherein the monomers or prepolymers are selected from the group consisting of vinylidene chloride, chloropene, isoprene, dimethylaminoethyl methacrylate, styrene, 1,3-butylene dimethacrylate, hydroxyethyl methacrylate, isoctylvinyl ether, acrylonitrile, acrylamide, N-vinyl pryridine, glycidyl methacrylate, N-vinyl caprolactam, N-vinyl pyrrolidone, N-vinyl carbazole, acrylic acid, methacrylic acid, ethyl acrylate, ethyl methacrylate, itaconic acid, isobutylmethacrylate, methyl acrylate, sodium styrene sulfonate, sodium vinyl sulfonate, bis(-beta-chloroethyl) vinyl phosphate, cetyl vinyl ether, divinylether of ethylene glycol, divinyl ether of butanediol, vinyl toluene, vinyl acetate, octadecyl vinyl ether.

15. The method of claim 1, wherein the monomers or prepolymers have a concentration of between about 5% and 15% by weight of the polymerizable composition.

16. The method of claim 2, wherein the alkali metal hydroxide is selected from the group consisting of sodium hydroxide, potassium hydroxide and lithium hydroxide.

17. The method of claim 16, wherein the alkali metal hydroxide has a concentration of between about 0.5% and 5% by weight of the graft activating solution.

* * * * *